United States Patent [19]

Gaughan et al.

[11] 4,356,025

[45] Oct. 26, 1982

[54] N-(BENZENESULFONYL) THIOCARBAMATES - HERBICIDAL ANTIDOTES

[75] Inventors: Edmund J. Gaughan, Berkeley; Charles Kezerian, Orinda, both of Calif.

[73] Assignee: Stauffer Chemical Company, Westport, Conn.

[21] Appl. No.: 241,278

[22] Filed: Mar. 6, 1981

Related U.S. Application Data

[60] Division of Ser. No. 108,890, Dec. 31, 1979, Pat. No. 4,297,295, which is a division of Ser. No. 723,251, Sep. 17, 1976, abandoned, which is a continuation-in-part of Ser. No. 619,115, Oct. 2, 1975, abandoned.

[51] Int. Cl.³ .............................................. A01N 37/00
[52] U.S. Cl. .................................................... 71/100
[58] Field of Search ............................ 71/103, 100, 88

[56] References Cited

U.S. PATENT DOCUMENTS

| | | | |
|---|---|---|---|
| 2,384,577 | 9/1945 | Thomas | 260/455 A |
| 2,992,091 | 7/1961 | Harman et al. | 71/101 |
| 3,124,447 | 3/1964 | Wineman et al. | 71/103 |
| 3,131,509 | 5/1964 | Hoffmann | 71/77 |
| 3,628,945 | 12/1971 | Doyle, Jr. | 260/455 A |
| 3,742,007 | 6/1973 | Osieka et al. | 71/101 |
| 3,799,760 | 3/1974 | Stephens | 71/103 |
| 3,810,928 | 5/1974 | Brown | 260/455 A |
| 3,823,008 | 7/1974 | Carpenter et al. | 71/103 |
| 3,885,039 | 5/1975 | Pinkowski et al. | 260/455 A |
| 4,071,353 | 1/1978 | Arneklev et al. | 71/100 |

OTHER PUBLICATIONS

Kriesel et al., "Synthesis and Pharmacological, etc.", (1968), Index Chemicus 32, No. 105938 (1969).

Hirooka et al., "Synthesis and Reactions, etc.", (1970), CA 73, No. 14369w, (1970).

*Primary Examiner*—Glennon H. Hollrah
*Attorney, Agent, or Firm*—Harry A. Pacini

[57] ABSTRACT

N-(substituted and unsubstituted benzenesulfonyl) thiocarbamates as new compositions of matter useful as active herbicidal antidotes to protect various crops from injury when used with a thiocarbamate herbicide; improved herbicidal compositions and utility of said compositions employing N-benzenesulfonyl thiocarbamates having the formula

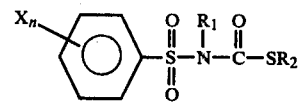

wherein X is hydrogen, methyl, chloro, bromo, or methoxy; n is an interger 1 to 3, inclusive; $R_1$ is hydrogen or methyl; and $R_2$ is alkyl having from 1 to 4 carbon atoms, inclusive, methylthio-p-chlorobenzenesulfonyl carbamate, benzyl or 4-chlorophenyl; provided that when X is hydrogen and $R_1$ is methyl, the $R_2$ is other than ethyl.

42 Claims, No Drawings

N-(BENZENESULFONYL) THIOCARBAMATES - HERBICIDAL ANTIDOTES

This is a division of application Ser. No. 108,890, filed Dec. 31, 1979 now U.S. Pat. No. 4,297,295, which application is a division of Ser. No. 723,251, filed Sept. 17, 1976, now abandoned, which is a continuation-in-part application of copending application Ser. No. 619,115, filed Oct. 2, 1975, now abandoned.

BACKGROUND OF THE INVENTION

While many herbicides are immediately toxic to a large number of weed pests, it is known that the effect of many herbicides upon important plant cultivations is either non-selective or not adequately selective. Thus, many herbicides damage not only the weeds to be controlled but, to a greater or lesser extent, the desirable cultivated plants as well. This holds true for many herbicidal compounds which have been commercially successful and are commercially available. These herbicides include types such as triazines, urea derivatives, halogenated acetanilides, carbamates, thiocarbamates and the like. Some examples of these compounds are described in U.S. Pat. Nos. 2,913,327, 3,037,853, 3,175,897, 3,185,720, 3,198,786 and 3,582,314.

The side effect of injury to a cultivated crop by various herbicides is particularly inconvenient and unfortunate. When used in the recommended amounts in the soil to control broadleaf weeds and grasses, serious malformation or stunting of the crop plants sometimes result. This abnormal growth in the crop plants results in loss of crop yield. The search continues for good selective herbicides.

Previous attempts are described to overcome this problem. The treatment of the crop seed with certain "hormonal" antagonistic agents prior to planting is described; see U.S. Pat. Nos. 3,131,509 and 3,564,768. The protective agents, as well as the herbicides, in these prior processes are largely specific to certain cultivated plant species or in the nature of the antagonistic agents. The prior antagonistic agents have not been notably successful. The aforementioned patents specifically exemplify and describe the treatment of seeds employing compounds of a different chemical class, not suggestive of the present invention.

The literature describes the preparation of certain N-(benzenesulfonyl) thiocarbamates for which no utility is disclosed. The reference, Hirooka et al., Nippon Kagaku Zasshi: 1970, 91(3) 270(5), CA 73:14369w (1970), relates to the synthesis and reactions of bis-[N-(phenylsulfonyl)-formimidoyl]disulfides. From certain reactions of an appropriate disulfide with hydrogen peroxide, there is obtained N-(phenylsulfonyl)methyl thiolcarbamates. Further, there is reference to certain alkyl p-toluenesulfonylthiocarbamates used in pharmacological evaluations. These latter compounds are by Kriesel, D. C. et al., J. Pharm Sci., 1968, 57(10), 1791-3.

DESCRIPTION OF THE INVENTION

It has been discovered that cultivated crop plants can be protected against injury by thiocarbamate-type herbicides, alone or in mixtures or combination with other compounds. Further, as an alternative effect, the tolerance of growing plants, more particularly soybeans, to the thiocarbamate herbicides, more particularly S-n-propyl N,N-di-n-propylthiocarbamate, can be increased substantially by adding to the soil compound of the type N-(substituted and unsubstituted benzenesulfonyl) thiocarbamate which is an effective antidote with said thiocarbamate herbicide, said compound corresponding to the following formula

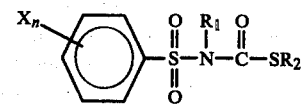

wherein X is hydrogen, methyl, chloro, bromo or methoxy; n is an interger from 1 to 3, inclusive, $R_1$ is hydrogen or methyl; and $R_2$ is alkyl having from 1 to 4 carbon atoms, inclusive, methylthio-p-chlorobenzenesulfonyl carbamate, benzyl or 4-chlorophenyl; provided that when X is hydrogen and $R_1$ is methyl, then $R_2$ is other than ethyl.

As a preferred embodiment of the present invention, is a two part herbicide system comprising (1) a first part consisting of at least one thiocarbamate herbicide and (2) a second part consisting of at least one compound having the formula

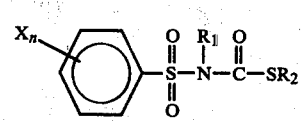

wherein X is hydrogen, methyl, chloro, bromo, or methoxy; n is an interger from 1 to 3 inclusive, $R_1$ is hydrogen or methyl; and $R_2$ is alkyl having from 1 to 4 carbon atoms, inclusive, methylthio-p-chlorobenzenesulfonyl carbamate, benzyl or 4-chlorophenyl; provided that when X is hydrogen and $R_1$ is methyl, then $R_2$ is other than ethyl; said compound being antidotally active with said thiocarbamate herbicide.

Certain of the compounds disclosed herein are considered new compositions of matter and correspond to the following formula

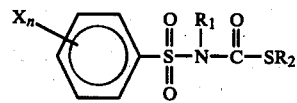

wherein X is hydrogen, methyl, chloro, bromo or methoxy; n is an interger from 1 to 3, inclusive, $R_1$ is hydrogen or methyl; and $R_2$ is alkyl having from 2 to 4 carbon atoms, inclusive, methylthio-p-chlorobenzenesulfonyl carbamate, benzyl or 4-chlorophenyl; provided that when X is methyl, then $R_2$ is other than alkyl and provided that when X is hydrogen and $R_1$ is methyl, then $R_2$ is other than ethyl.

In the above descriptions, the following embodiment is intended for the various alkyl substituent groups. As exemplary of the alkyl portion within the preferred embodiment are the following: Methyl, ethyl, n-propyl, isopropyl, n-butyl, sec.-butyl, isobutyl, and tert.-butyl. Whereas n can be an interger from 1 to 3, inclusive, preferably n is 3 when X is methyl; and n is a parasubstitution of the X moiety.

As an alternative mode of action, the compounds of this invention may interfere with the normal herbicidal action of the thiocarbamate-type and other herbicides to render them selective in their action. Whichever mode of action is present, the corresponding beneficial and desirable effect is the continued herbicidal effect of the thiocarbamate with the accompanying decreased herbicidal effect on desired crop species. This advantage and utility will become more apparent hereinafter.

Therefore, the terms "herbicide antidote" or "antidotal amount", is meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the soil in which a crop is planted. Hitherto, there have been no systems which have been satisfactory for this purpose.

The compounds of this invention represented by the above formulas can be prepared by several different procedures depending upon the starting materials.

The appropriate intermediate, arylsulfonamide, was reacted with an alkyl chlorothiolformate in the presence of a hydrogen chloride acceptor to prepare the desired compound. Work-up and purification procedures involved standard methods of extraction, distillation or crystallization. In most instances, characterization of the structure was by infrared spectroscopy, nuclear magnetic resonance or mass spectroscopy, as well as physical constants.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE I

Preparation of N-(p-methoxybenzenesulfonyl)-ethyl thiolcarbamate p-Methoxybenzenesulfonamide (11.7 g., 0.64 mole), potassium carbonate (21.5 g., 0.156 mole), and ethyl chlorothiolformate (8.5 g., 0.068 mole) were refluxed in 80 ml. of acetone for eight hours. The cooled mixture was poured into 350 ml. water and the solution filtered through Celite and extracted with benzene to remove any unreacted chlorothiolformate. It was then acidified with hydrochloric acid (pH about 2) with cooling. The mixture was extracted with benzene and the extract washed with water and dried over magnesium sulfate. Removal of the solvent left the product as a very viscous oil. There was obtained 8.4 g. (48% theory) of the title compound, $n_D^{30}$ 1.5502.

EXAMPLE II

Preparation of N-(p-chlorobenzenesulfonyl)-ethyl thiolcarbamate p-Chlorobenzenesulfonamide (12.0 g., 0.063 mole), potassium carbonate (21.5 g., 0.156 mole), and ethyl chlorothiolformate (8.5 g., 0.068 mole) were refluxed in 75 ml. of acetone for six hours. The work-up was as in Example I. The crude product was triturated with hexane and dried. There was obtained 12.4 g. (70% of theory) of the title compound, m.p. 93°–95° C. The structure was confirmed by infrared, nuclear magnetic resonance, and mass spectroscopy.

EXAMPLE III

Preparation of N-(benzenesulfonyl)-ethyl thiolcarbamate

Benzenesulfonamide (39.3 g., 0.25 mole), and potassium carbonate (90 g., 0.65 mole) were placed in 300 ml. of acetone and ethyl chlorothiolformate (41 g., 0.33 mole) added over several hours. The mixture was stirred one hour at room temperature, then refluxed 12 hours. It was cooled, poured into one l. of water and acidified with 100 ml. hydrochloric acid. The product was extracted with 250 ml. benzene and the extract dried over magnesium sulfate. It was filtered and the solvent removed. Pentane (100 ml.) was added, whereupon the product crystallized. It was filtered, washed with 50 ml. pentane, and dried at 50° C. There was obtained 58 g. (95% of theory) of the title compound, m.p. 100°–103° C. Analysis: N, calculated, 5.72; found, 5.59; Analysis: S, calculated, 26.1; found, 26.24.

EXAMPLE IV

Preparation of N-(p-chlorobenzenesulfonyl)-p-chlorophenyl thiolcarbamate p-Chlorobenzenesulfonamide (19.1 g., 0.1 mole), potassium carbonate (30 g., 0.22 mole), and p-chlorophenyl chlorothiolformate (22 g., 0.11 mole) in 150 ml. acetone were refluxed and stirred for 10.5 hours. The cooled mixture was poured into one liter water and acidified with acetic acid. The precipitate was filtered, washed with water and dried. There was obtained 20 g. (55.5% of theory) of the title compound, m.p. 129°–132° C.

Analysis: N, calculated 3.85; found, 4.83.
Analysis: S, calculated, 17.67; found, 17.37.

The following is a table of the compounds which are prepared according to the aforementioned procedures. Compound numbers have been assigned to them and are used for identification throughout the balance of the specification.

TABLE I

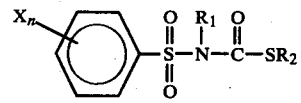

| COMPOUND NUMBER | n | x | $R_1$ | $R_2$ | m.p. °C. or $n_D^{30}$ |
|---|---|---|---|---|---|
| 1 | 1 | para-$CH_3$ | H | $C_2H_5$ | 104–110 |
| 2 | 1 | H | H | $C_2H_5$ | 100–103 |
| 3 | 1 | para-Cl | H | 4-Cl—φ | 129–132 |
| 4 | 1 | para-Cl | $CH_3$ | $C_2H_5$ | 1.5643 |
| 5 | 1 | para-Cl | H | $C_2H_5$ | 93–95 |
| 6 | 1 | para-Br | H | $C_2H_5$ | 102–107 |

TABLE I-continued

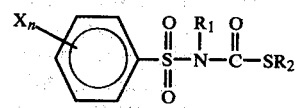

| COMPOUND NUMBER | n | x | $R_1$ | $R_2$ | m.p. °C. or $n_D^{30}$ |
|---|---|---|---|---|---|
| 7 | 1 | para-Cl | H | n-$C_3H_7$ | 94–96 |
| 8 | 1 | para-Cl | H | i-$C_3H_7$ | 77–83 |
| 9 | 1 | para-$OCH_3$ | H | $C_2H_5$ | 1.5502 |
| 10 | 1 | para-Cl | H | $CH_2\phi$ | 94–96 |
| 11 | 3 | 2,4,6-$CH_3$ | H | $C_2H_5$ | 105–108 |
| 12 | 1 | para-Cl | H | $CH_2SC(O)S(O_2)$—4-Cl$\phi$ | 238–239 dec. |

The herbicide indicated in the tables and elsewhere are used at rates which produce effective control of undesirable vegetation. The range of rates employed herein produce representative results within the recommended amounts set forth by the supplier. Therefore, the weed control in each instance is commercially acceptable within the desired or recommended amount.

It is clear that the class of herbicidal agents described and illustrated herein is characterized as an effective herbicide exhibiting such activity. The degree of this herebicidal activity varies among specific compounds and among combinations of specific compounds within the class. Similarly, the degree of activity to some extent varies among the species of plants to which a specific herbicidal compound or combination may be applied. Thus, selection of a specific herbicidal compound or combination to control undesirable plant species readily may be made. Within the present invention, the prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with no discrimination between desirable and undesirable species. The method of controlling vegetation compries applying an herbicidally effective amount of the herein described herbicidal compounds to the area or plant locus where control is desired. The compositions as set forth in this invention include those wherein the preferred active thiocarbamate herbicidal compound is preferably S-n-propyl N,N-di-n-propyl thiocarbamate.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants", it is meant germinant seeds, emerging seedlings and established vegetation including the roots and aboveground portions.

Evaluation Procedures

Flats to be used for growing the crops and weed species were filled with loamy sand soil. Stock solutions of the herbicide and each candidate antidote were prepared as follows:

A. Herbicide—S-n-propyl, N,N-di-n-propyl thiocarbamate—VERNAM® 6E—1560 mg. of VERNAM 6E was diluted in 250 ml. of water so that 5 ml. applied to a flat is equivalent to 6 lb/A per flat (based) on the surface area of a flat).

B. Antidote—of each candidate 78 mg. was dissolved in 20 ml. of acetone with 1% Tween 20® (polyoxyethylene sorbitan monolaurate) so that 5 ml. when applied by pre-plant incorporation technique (PPI) is equal to 5 lb/A per flat.

The herbicide and antidotes were applied to the soil together as a tank mix employing pre-plant incorporation technique. To prepare the combined tank mix, 5 ml. of the VERNAM® stock solution and 5 ml. of each of the antidote stock solutions were admixed, followed by incorporation into the soil from the flats during incorporation in a rotary mixer.

One row each of the following weeds and crop was seeded into the treated soil in the flats:
Watergrass (*Echinochloa crusgalli*);
Foxtail (*Sataria viridis*); and
Soybeans (*Glycine max*)

The flats were placed on greenhouse benches where temperatures were maintained between 70°–90° F. The soil was watered by sprinkling to assure good plant growth. Injury ratings were taken 2 and 4 weeks after the application was made. Individual flats treated with the herbicide alone were included to provide a basis for determining the amount of injury reduction provided by the herbicide antidotes.

The following table includes results as percent protection for the crop according to the procedures discussed above. The percent protection is determined by a comparison with flats not treated with the candidate antidotes of this invention.

TABLE II

| Application Method: | Pre-plant Incorporation - PPI (Tank Mix) | | |
|---|---|---|---|
| Crop Species: | Soybeans (Glycine max) | | |
| Weed Species: | Foxtail (Sataria viridis) | | |
| | Watergrass (Echinochloa crusgalli) | | |
| COMPOUND | PPI (6 lb/A) (Tank Mix) | | |
| NUMBER | Soybeans | Watergrass | Foxtail |
| VERNAM 6 lb/A | 40* | 100* | 100* |
| 1** | 37.5 | 0 | 0 |
| 2 | 37.5 | 0 | 0 |
| 3 | 25 | 0 | 0 |
| 4 | 25 | 0 | 0 |
| 5 | 50 | 0 | 0 |
| 6 | 25 | 0 | 0 |
| 7 | 25 | 0 | 0 |
| 8 | 50 | 0 | 0 |
| 9 | 25 | 0 | 0 |
| 10$^a$ | 75 | 0 | 0 |
| 11 | 33 | 0 | 0 |

TABLE II-continued

Application Method: Pre-plant Incorporation - PPI (Tank Mix)
Crop Species: Soybeans (Glycine max)
Weed Species: Foxtail (Sataria viridis)
Watergrass (Echinochloa crusgalli)

| COMPOUND NUMBER VERNAM 6 lb/A | PPI (6 lb/A) (Tank Mix) | | |
|---|---|---|---|
| | Soybeans 40* | Watergrass 100* | Foxtail 100* |
| 12 | 50 | 0 | 0 |

$^a$= Pre-plant incorporation of VERNAM ® and antidote applied separately to soil prior to incorporation.
*= % injury
**= % protection The thiocarbamate herbicide S-ethyl cyclohexylethyl thiocarbamate and compound number 6 when applied to the soil together as a tank mix employing pre-plant incorporation technique, exhibited 50 percent protection to grain sorghum (milo) planted in the treated soil. That is, the injury to emerging grain sorghum plants was decreased by at least 50 percent when grown in soil treated with a tank mix of compound number 6 and S-ethyl cyclohexylethyl thiocarbamate. This is compared to grain sorghum (milo) planted in soil containing a treatment of only the thiocarbamate herbicide.

Various other varieties of legumes were tested for antidote activity in conjunction with a representative thiocarbamate herbicide and a N-(benzenesulfonyl) thiocarbamate. Legumes are plants that have a symbiotic relationship with nitrogen fixing organisms. For example, soybeans, varieties of phaeolus vulgarius, peanuts, alfalfa, cloves, peas and the like.

The antidote candidate from the above list of N-(benzenesulfonyl) thiocarbamates compound number 5 was used at the rates of 1 and 2 lb/A. The stock solution used consisted of 39 mg. dissolved in 25 ml. of acetone, such that 2.5 ml. is equivalent to 1 lb/A when applied pre-plant incorporated. The representative thiocarbamate herbicide was EPTC, S-ethyl N,N-dipropyl thiocarbamate. The herbicide stock solution was made up by dissolving 1560 mg. of EPTC 6E in 250 ml. water, such that 5 ml. of solution was equivalent to 6 lb/A when pre-plant incorporated in the soil.

Navy beans and pinto beans were evaluated in this test. Also present in the planted flats were the weed species, watergrass and foxtail. The results were rated at two and four weeks after treatment and seeding. After two weeks EPTC at 6 lb/A with 1 lb/A and 2 lb/A compound number 5 present injured only 10 percent of the navy beans and 0 percent of the pinto bean plants. After four weeks at 1 lb/A navy bean plants were protected 23 percent and pinto bean plants were protected 40 percent. At 2 lb/A after four weeks navy beans were protected 23 percent and pinto beans 20 percent. The watergrass and foxtail weeds species were completely (100 percent) controlled four weeks after treatment with the antidote and herbicide.

Seed Treatment Test

Small flats were filled with Felton loamy sand soil. Soil incorporated herbicides were applied at this time. The soil from each flat was placed into a five-gallon cement mixer where the soil was mixed as the herebicides were applied using a predetermined amount of a stock solution containing 780 mg. of approximately 75 percent active ingredient to 125 ml. of water. Five ml. of stock solution was applied to the soil in a volumetric pipet. Five ml. of stock solution contained an equivalent of herbicide which equals to six pounds per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, soybean (Glycine max) seeds were planted in each row. Rows were approximately one and one-half inches apart in the flat. Seeds were treated by preparing a stock solution by dissolving 250 mg. of the antidote compound in 2.5 ml. of acetone, then using 0.5 ml. of the stock solution to treat 10 g. of soybean seed equivalent to 0.5 percent w/w. Antidote compounds can also be applied as liquid slurries and powders or dusts. In some cases, acetone is used to dissolve powdered or solid compounds so they could be more effectively applied to the seeds.

After the flats were seeded, they were covered with the one pint of soil which had been removed just prior to planting. Flats were placed on greenhouse benches were temperatures ranged from 70°-90° F. Flats were watered by sprinkling as needed to assure good plant growth. Percent control ratings were taken four weeks after the treatments were applied.

In each test, the herbicide was applied alone, in combination with the seed protectant, and the seed protectant was applied alone to check for phytotoxocity. The untreated adjacent row was employed to observe any beneficial lateral movement of the antidote compound through the soil. The degree of the effect was noted by comparison with the control.

In this seed treatment test with the herbicide S-n-propyl N,N-di-n-propyl thiocarbamate, compound number 5 exhibited 50 percent protection to the treated soybean seeds. That is, the injury was reduced by at least 50 percent to the emerging soybean plants grown from seed treated with compound number 5 compared to untreated seed grown in soil containing the thiocarbamate herbicide.

The compounds and compositions of this invention were employed in effective herbicidal compositions comprising the antidote and a representative thiocarbamate herbicide as described hereinabove. The herbicidal compositions were tested in the following manner.

The compositions of the present invention for the protection of cultivated crop plants comprise an active herbicidal compound and an antidote therefor selected from the above-described compounds. The compositions of herbicide and antidote can be prepared by conventional methods through the thorough mixing and grinding of the active herbicide agents and the antidote with suitable carriers and/or other distribution media, possibly with the addition of dispersion agents or solvents.

The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.001 to about 30 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

What is claimed is:

1. A herbicidal composition consisting essentially of an effective amount of a thiocarbamate herbicide and an antidotally effective amount of a compound corresponding to the formula

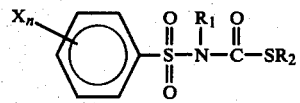

in which X is hydrogen, methyl, chloro, bromo, or methoxy; $R_1$ is hydrogen or methyl; and $R_2$ is alkyl having from 1 to 4 carbon atoms, inclusive, methylthio-p-chlorobenzene sulfonyl carbamate, benzyl or 4-chlorophenyl; provided that when X is hydrogen and $R_1$ is methyl, then $R_2$ is other than ethyl; said compound being antidotally active with said thiocarbamate herbicide.

2. The herbicidal composition according to claim 1 in which X is para-methyl, $R_1$ is hydrogen and $R_2$ is alkyl.

3. The herbicidal composition according to claim 2 in which $R_2$ is ethyl.

4. The herbicidal composition according to claim 1 in which X is hydrogen, $R_1$ is hydrogen and $R_2$ is alkyl.

5. The herbicidal composition according to claim 4 in which $R_2$ is ethyl.

6. The herbicidal composition according to claim 1 in which X is para-chloro, $R_1$ is hydrogen and $R_2$ is 4-chlorophenyl.

7. The herbicidal composition according to claim 1 in which X is para-chloro, $R_1$ is methyl and $R_2$ is alkyl.

8. The herbicidal composition according to claim 7 in which $R_2$ is ethyl.

9. The herbicidal composition according to claim 1 in which X is para-chloro, $R_1$ is hydrogen and $R_2$ is alkyl.

10. The herbicidal composition according to claim 9 in which $R_2$ is ethyl.

11. The herbicidal composition according to claim 9 in which $R_2$ is n-propyl.

12. The herbicidal composition according to claim 9 in which $R_2$ is isopropyl.

13. The herbicidal composition according to claim 1 in which X is para-methoxy, $R_1$ is hydrogen and $R_2$ is alkyl.

14. The herbicidal composition according to claim 13 in which $R_2$ is ethyl.

15. The herbicidal composition according to claim 1 in which X is para-chloro, $R_1$ is hydrogen and $R_2$ is benzyl.

16. The herbicidal composition according to claim 1 in which X is para-bromo, $R_1$ is hydrogen and $R_2$ is alkyl.

17. The herbicidal composition according to claim 16 in which $R_2$ is ethyl.

18. The herbicidal composition according to claim 1 in which X is para-chloro, $R_1$ is hydrogen and $R_2$ is methylthio-p-chlorobenzene sulfonyl carbamate.

19. The herbicidal composition according to claim 1 in which $X_n$ is 2,4,6-methyl, $R_1$ is hydrogen and $R_2$ is alkyl.

20. The herbicidal composition according to claim 1 in which $R_2$ is ethyl.

21. The method of protecting soybean crops from injury, said injury due to the thiocarbamate herbicide S-n-propyl di-n-propylthiocarbamate, comprising application to the soil in which said crop is to be planted and grown, non-phytotoxic antidotally effective amount of a compound corresponding to the formula

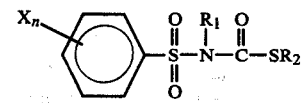

in which X is hydrogen, methyl, chloro, bromo, or methoxy; $R_1$ is hydrogen or methyl; and $R_2$ is alkyl having from 1 to 4 carbon atoms, inclusive, methylthio-p-chlorobenzene sulfonyl carbamate, benzyl or 4-chlorophenyl; provided that when X is hydrogen and $R_1$ is methyl, then $R_2$ is other than ethyl.

22. The method according to claim 21 in which X is para methyl, $R_1$ is hydrogen and $R_2$ is alkyl.

23. The method according to claim 22 in which $R_2$ is ethyl.

24. The method according to claim 21 in which X is hydrogen, $R_1$ is hydrogen and $R_2$ is alkyl.

25. The method according to claim 24 in which $R_2$ is ethyl.

26. The method according to claim 21 in which X is parachloro, $R_1$ is hydrogen and $R_2$ is 4-chlorophenyl.

27. The method according to claim 21 in which X is parachloro, $R_1$ is methyl and $R_2$ is alkyl.

28. The method according to claim 27 in which $R_2$ is ethyl.

29. The method according to claim 21 in which X is parachloro, $R_1$ is hydrogen and $R_2$ is alkyl.

30. The method according to claim 29 in which $R_2$ is ethyl.

31. The method according to claim 29 in which $R_2$ is n-propyl.

32. The method according to claim 29 in which $R_2$ is isopropyl.

33. The method according to claim 21 in which X is para methoxy, $R_1$ is hydrogen and $R_2$ is alkyl.

34. The method according to claim 33 in which $R_2$ is ethyl.

35. The method according to claim 21 in which X is para-chloro, $R_1$ is hydrogen and $R_2$ is benzyl.

36. The method according to claim 21 in which X is parabromo, $R_1$ is hydrogen and $R_2$ is alkyl.

37. The method according to claim 36 in which $R_2$ is ethyl.

38. The method according to claim 21 in which X is parachloro, $R_1$ is hydrogen and $R_2$ is methylthio-p-chlorobenzene sulfonyl carbamate.

39. The method according to claim 21 in which $X_n$ is 2,4,6-methyl, $R_1$ is hydrogen and $R_2$ is alkyl.

40. The method according to claim 39 in which $R_2$ is ethyl.

41. The herbicidal composition as set forth in claim 1 wherein said thiocarbamate herbicide is selected from the group S-n-propyl N,N-di-n-propyl thiocarbamate, S-ethyl dipropyl thiocarbamate, and S-ethyl cyclohexylethyl thiocarbamate.

42. The method of protecting a crop from injury, said injury due to a thiocarbamate herbicide selected from the group S-n-propyl N,N-di-n-propyl thiocarbamate, S-ethyl dipropyl thiocarbamate, and S-ethyl cyclohexylethyl thiocarbamate; comprising application to the soil in which an herbicidally effective amount of said thiocarbamate is used, a non-phytotoxic amount of a compound corresponding to the formula

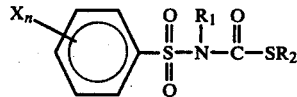

in which X is hydrogen, methyl, chloro, bromo, or methoxy; $R_1$ is hydrogen or methyl; and $R_2$ is alkyl having from 1 to 4 carbon atoms, inclusive, methylthio-p-chlorobenzene sulfonyl carbamate, benzyl or 4-chlorophenyl; provided that when X is hydrogen and $R_1$ is methyl, then $R_2$ is other than ethyl; said compound being antidotally active with said thiocarbamate herbicide.

* * * * *